United States Patent [19]
Collings et al.

[11] Patent Number: 5,952,560
[45] Date of Patent: Sep. 14, 1999

[54] PARTICLE PROPERTY MEASUREMENT

[75] Inventors: Anthony F Collings, Turramurra; Nicholas Bajenov, Wahroonga; Peter John Cusack, Mount Colah, all of Australia

[73] Assignee: Commonwealth Scientific and Industrial Research Organisation, Campbell, Australia

[21] Appl. No.: 08/836,838

[22] PCT Filed: Nov. 9, 1995

[86] PCT No.: PCT/AU95/00747

§ 371 Date: Jul. 17, 1997

§ 102(e) Date: Jul. 17, 1997

[87] PCT Pub. No.: WO96/15446

PCT Pub. Date: May 23, 1996

[30] Foreign Application Priority Data

Nov. 9, 1994 [AU] Australia .................................... 9349

[51] Int. Cl.⁶ ....................................................... G01N 29/02
[52] U.S. Cl. ............................... 73/61.75; 73/599; 73/600
[58] Field of Search ...................... 73/61.75, 599, 73/600

[56] References Cited

U.S. PATENT DOCUMENTS

| | | |
|---|---|---|
| 3,779,070 | 12/1973 | Cushman et al. . |
| 4,202,215 | 5/1980 | Meyer ........................................ 73/599 |
| 4,414,850 | 11/1983 | Miwa et al. ............................... 73/599 |
| 4,509,524 | 4/1985 | Miwa ......................................... 73/597 |
| 4,594,896 | 6/1986 | Cardoso et al. . |
| 4,688,428 | 8/1987 | Nicolas . |
| 4,750,366 | 6/1988 | Nicolas . |

FOREIGN PATENT DOCUMENTS

| | | | |
|---|---|---|---|
| A-91757/82 | 12/1982 | Australia | ............................... 73/61.75 |
| 2 707 112 | 6/1993 | France . | |
| 91/007646 | 5/1991 | WIPO . | |
| 93/16640 | 9/1993 | WIPO . | |

*Primary Examiner*—Daniel S. Larkin
*Attorney, Agent, or Firm*—Rockey, Milnamow & Katz, Ltd.

[57] ABSTRACT

A method and apparatus for the measurement of a property of particles suspended in a medium are described. In one embodiment, the deformability of sampled red blood cells is measured. A pulse generator (40) provides a narrow square pulse to a transmitting transducer (35), which passes an ultrasonic wave through the sample medium (15) to be received by a receiving transducer (36). The output signal from the transducer (36) is amplified by an amplifier (41) then subjected to signal processing. The acoustic absorption of the sample is calculated and scaled with frequency. The slope of a plot of scaled absorption with frequency gives a measure of the red blood cells' deformability.

17 Claims, 9 Drawing Sheets

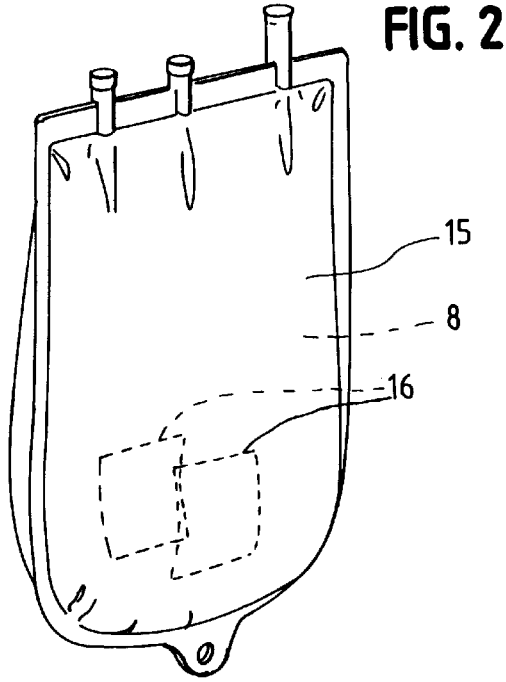
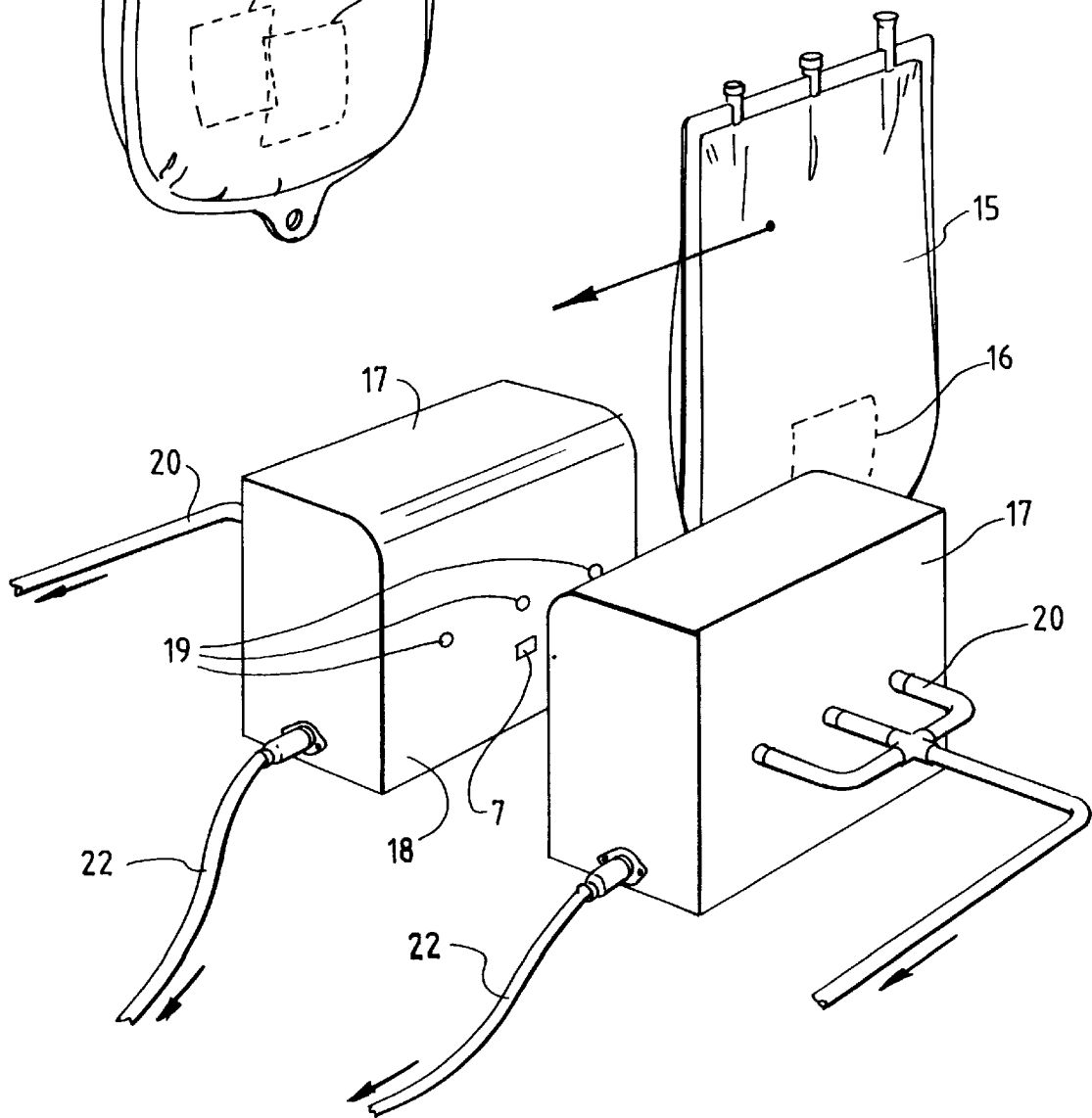

PARTICLE PROPERTY MEASUREMENT

FIELD OF THE INVENTION

The present invention relates to the measurement of the properties of particles suspended in a medium, where the medium can be a solid or a liquid. The present invention is particularly applicable to the measurement of the deformability of suspended red blood cells in whole or fractionated blood.

BACKGROUND OF THE INVENTION

Even in those countries where blood is donated free of charge, as opposed to being purchased, the need to type, screen against various diseases and refrigerate the blood for storage means that there are substantial expenses involved in the making of blood available for use within the health care system. An estimate of the actual cost of supplying a unit (450 ml) of blood is in the vicinity of $A250.00 and approximately 300,000 blood units are used each year in a city such as Sydney, Australia, having a population of 3.5 million. In this connection, the term "blood" is used in relation to blood and blood-like or blood-derived liquids including suspensions of red blood cells (erythrocytes) in saline solution. Such blood-like or blood-derived liquids are in substantial demand for open-heart surgery, car accident victims, difficult births, and like medical procedures.

The ability of blood to be stored depends in large part upon the "life" of the red blood cells within the blood sample. In clinical terms, the poor condition of red blood cells is known as the lack of deformability, the converse of which is known as 'brittleness'. The average red blood cell is 7.5 $\mu$m in diameter, and in order to pass down capillaries (that are as small as 3 $\mu$m) they must readily deform. The inability to deform can reduce the efficiency of circulation. Abnormal deformability has been linked to diseases as varied as sickle cell anaemia and diabetes. It would thus be useful to be able to quickly perform a measurement on a small sample of a person's blood to determine red blood cell deformability and hence the condition of the blood.

Red blood cell deformability increases with the level of fitness in trained athletes, and thus the ability to perform quick measurements of red cell deformability would prove a useful tool to assist in fitness assessment.

There is considerable variability from person to person and from sample to sample so far as blood "shelf-life" is concerned. In some instances, degradation sets in within three to six days, while in other instances there is no appreciable loss of condition in a period up to ten weeks. In the absence of a suitable testing regime, units of blood are normally kept for between three and seven weeks before being discarded at the end of this period if not used.

It is highly desirable that the cost of production of a stock of blood be able to be amortised over a longer period of time, perhaps up to two months, in order to reduce the effective cost of the availability of blood samples. The amortisation period can be increased if the storage period can be increased. The storage period can be increased if a simple and effective test is available which enables a determination to be made as to whether a specific blood sample is of a condition above some suitable minimum condition. If such a test were available, only those blood samples which have actually deteriorated would be quickly discarded, instead of discarding all blood samples on the basis of the "storage life" of those samples which deteriorate fastest.

A particular problem in relation to blood is that once a sample has been sealed within a sterile container, it is highly desirable to maintain the sterility. In order, therefore, to provide a low cost testing method in relation to blood and other such liquids which must be maintained under sterile conditions, it is highly desirable that the test can be applied to the sealed container without breaking the seal in any way. In this way the possibility of contaminating the contents of the sample would be avoided.

It is known from Australian Patent No. 557,256 (which originated from one of the present inventors and is assigned to the present applicant) to measure the flexibility of red blood cells in a liquid suspension by means of passing an ultrasonic signal through the suspension, which is held within a carefully constructed cell. The deformability of red blood cells can be measured using the variation of the absorption of ultrasonic energy with frequency. The walls of the red blood cells have a mechanical relaxation time related to their deformability, and when ultrasound is propagated through blood, some energy is absorbed in deforming the walls due to the relaxation process. There is a near-linear relationship between $\alpha/f$ and f (where $\alpha$ is the absorption coefficient, and f is frequency).

The method is relatively time consuming in that a number of measurements must be taken at each frequency and also at a number of different frequencies in order to provide the desired results. In addition, laborious impedance matching must be carried out at each individual frequency. The cost of the equipment is approximately $A40–50,000, and the time for a measurement to be made is of the order of two hours, which is too long for use in a commercial blood bank or hospital.

FIG. 14 shows a plot of $\alpha/f$ versus f for five samples of blood in varying condition measured in accordance with the prior art technique discussed above.

In accordance with the prior art method, the blood must be located within the special cell. Therefore it is necessary to destroy the sterile barrier which surrounds a specific blood sample in order to test the sample. In the event therefore that the sample should prove to be satisfactory, it is necessary to re-package the sample and sterilise it again. Naturally this re-sterilisation adds substantially to the practical cost of this prior art method. For the above reasons, the method disclosed in the above mentioned Australian patent has not been used in practice and has not found any commercial success, but instead remains a laboratory research tool.

DISCLOSURE OF THE INVENTION

It is an object of the present invention to substantially overcome or ameliorate the above mentioned difficulties by the provision of a method of sensing a property of particles suspended in a medium, which method can be carried out sufficiently quickly to find commercial applicability.

In accordance with one aspect of the present invention, there is disclosed a method for measuring the deformability of particles suspended in a medium, said method comprising the steps of:

locating said medium between a pair of ultrasonic transducers spaced apart, (applying an input electrical signal to one of said transducers to transmit an ultrasonic signal through said medium, said input electrical signal comprising or containing a range of frequencies, receiving said ultrasonic signal with the other of said transducers to generate a resultant output electrical signal, and processing said output electrical signal to calculate n absorption coefficient values for the particles as a function of frequency ($\alpha_n(f_n)$), scaling the absorption coefficient values by the respective frequency ($\alpha_n(f_n)/f_n$), and, for at least two of said n points, calculating the ratio of the difference between the frequency-scaled absorption value and the difference between the respective frequency ($\Delta((f_n)/f)_{1,2}/\Delta f_{1,2}$).

In one preferred form, the input signal is a swept signal which is swept from one end of said range of frequencies to the other whilst applied to the one transducer.

In another preferred form, the input signal is a square pulse, the harmonic content of which contains the desired range of frequencies.

In the event that the method is used in respect of blood in an hygienically sealed flexible walled container, for example, the container is preferably formed from, or contains a window means of, an ultrasonically transparent material, and the container, or window means respectively is located between the transducers.

In accordance with another aspect of the present invention, there is disclosed an apparatus for measuring the deformability of particles suspended in a medium and comprising:

a pair of opposed spaced apart ultrasonic transducers, and between which a sample of said medium can be located, a signal generator for applying an input electrical signal to one of said transducers to transmit an ultrasonic signal through said medium, said input electrical signals comprising a range of frequencies, the propagated signal being received by the other of said transducers to generate an output electrical signal, and signal processing means for receiving the output electrical signal and for calculating n absorption coefficient values for the particles as a function of frequency ($\alpha_n(f_n)$), scaling the absorption coefficient values by the respective frequency ($\alpha_n(f_n)/f_n$), and calculating the ratio, for at least two of n said points, of the difference between the frequency-scaled absorption value and the difference between the respective frequency ($\Delta(\alpha(f)/f)_{1,2}/\Delta f_{1,2}$).

In specific relationship to hygienically sealed samples of liquid, a flexible wall container formed from, or containing a window means of, an ultrasonically transparent material, is disclosed.

In accordance with a still further aspect of the present invention, there is disclosed a syringe for use in the measurement of the deformability of suspended red blood cells, the syringe comprising a hollow needle connected to one end of a hollow barrel and a plunger extending into said barrel from the other end thereof, and further comprising a first transducer located internally of and proximate the needle end of the barrel and a second transducer carried on the plunger, the plunger being usable to draw up a sample of blood whereafter the transducers can be used to measure the acoustic absorption of the red blood cells from which the deformability can be determined.

In accordance with a still further aspect of the invention, there is disclosed a method for measuring the acoustic absorption of suspended red blood cells, the method comprising the steps of:

locating said red blood cells between a pair of ultrasonic transducers, applying an input electrical signal to one of said transducers to transmit an ultrasonic signal through said medium, said input electrical signal having a range of frequencies, receiving said ultrasonic signal with the other of said transducers to generate a resultant output electrical signal, and processing said output electrical signal to calculate the absorption coefficients, $\alpha$, for one or more frequencies, said absorption coefficients being inversely proportional to the separation of the transducers and proportional to the natural logarithm of the amplitude of said output electrical signal.

DESCRIPTION OF THE DRAWINGS

A number of embodiments of the present invention will now be described with reference to the drawings, in which:

FIG. 2 is a schematic perspective view of a blood sample bag, FIG. 3 is a schematic perspective view illustrating the bag of FIG. 2 being passed through a test apparatus of the first embodiment.

BEST MODE FOR PERFORMING THE INVENTION

Figure 1:
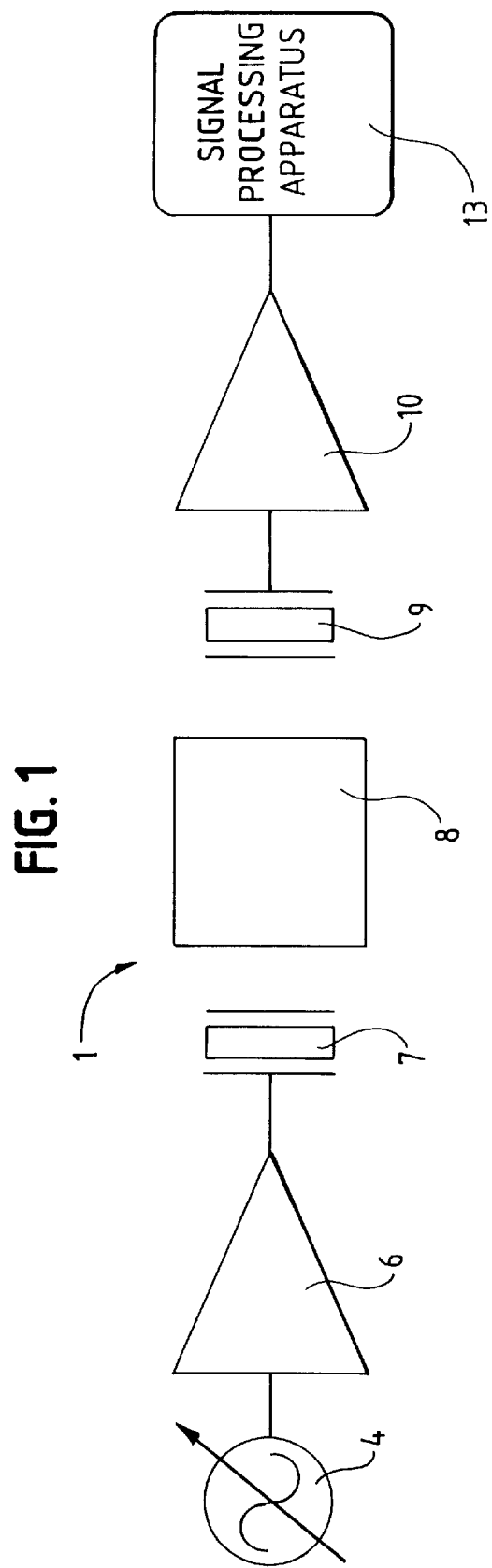
FIG. 1 is a circuit diagram of the electric circuit of test apparatus of the first embodiment.

The arrangement of the first embodiment is based upon the realisation that instead of performing a labour intensive measurement at each of a number of frequencies, it is possible to use a swept oscillator and thereby generate data and in a single measurement which covers a large range of frequencies. Accordingly, the electrical circuit 1 of the preferred embodiment takes the form of a variable frequency oscillator 4, the output of which is preferably generated in the range between approximately 0 to 100 MHz. The greater the frequency range, the greater the confidence in the subsequently derived value of deformability. This signal is applied to an amplifier 6, the output of which is connected to a first transducer 7. The transducer 7 is preferably a piezoelectric transducer, however other transducers are also able to be used.

The ultrasonic signal produced by the first transducer 7 passes through a blood sample 8 and is received by a second transducer 9. The output of the second transducer 9 is amplified by an amplifier 10 and then forms the input to signal processing apparatus 13.

The amplitude of the received signal is related to that of the transmitted signal by:

$$A_{rec} = k \cdot A_{elec} \cdot \exp(-\alpha(f) \cdot d) \quad\quad 1$$

where $A_{rec}$ is the amplitude of the received signal, k is the combined electrical to pressure coefficients of the transducers and the receiver amplifier gain, $A_{elec}$ is the amplitude of the electrical signal on the transmitting transducer, α(f) is the (frequency dependent) absorption coefficient, and d is the distance between the transducers 7,9.

The absorption coefficient α(f) at any frequency can then be calculated as:

$$\alpha(f) = -\frac{1}{d} \cdot \ln\left(\frac{A_{rec}}{k \cdot A_{elec}}\right) \qquad 2$$

From the amplitudes of the received signal at various frequencies, the absorption coefficient α(f) is calculated as:

$$\alpha(f) = \frac{1}{d} \cdot \ln(A_{rec}(f) \cdot C(f)) \qquad 3$$

where d is the distance between the transducers, $A_{rec}(f)$ is the amplitude of the received signal at each frequency, and C(f) is the correction function for the transducers, amplifier, cabling, and waveform shape at each frequency. The correction function C(f) is obtained by using distilled water (for example) as a reference medium. The quantity α(f)/f is then calculated at each frequency in the received signal. This quantity is then fitted to a linear function of frequency as:

$$A = \frac{\alpha(f)}{f} = m \cdot f + b \qquad 4$$

where m is the slope of the line of best fit and b is the offset. The slope m of the line is a measure of the deformability of the red cells (erythrocytes) in the blood sample.

As indicated in FIG. 2, the blood sample 8 is contained within a plastic bag 15. The bag 15 can be formed from conventional PVC or other biologically acceptable plastic material. The bag 15 is preferably manufactured from a material of low ultrasonic absorption, such as PVDF (polyvinylidene fluoride), or a material that may be considered substantially "ultrasonically transparent". Further, the thickness of the material can be optimised at λ/4 for the specific ultrasonic frequency. Alternatively, where spectral methods of absorption are used, a thickness significantly divergent from λ/4 can be used, and correction for that absorption in the bag can be performed in the convolution function. Alternatively, the bag 15 can include two opposed ultrasonically transparent windows 16 (illustrated in phantom) where the bag is formed from material that is not conducive to ultrasonic transmission.

As seen in FIG. 3, the bag 15 is passed between two housings 17 on the opposed front faces 18 of which the first and second transducers 7 and 9 are mounted so that the operating surface of each transducer 7, 9 is flush with the corresponding front face 18. In addition, the front faces 18 are each provided with several spaced apart apertures 19 which are preferably spaced apart and connected to corresponding vacuum lines 20.

Figure 4:
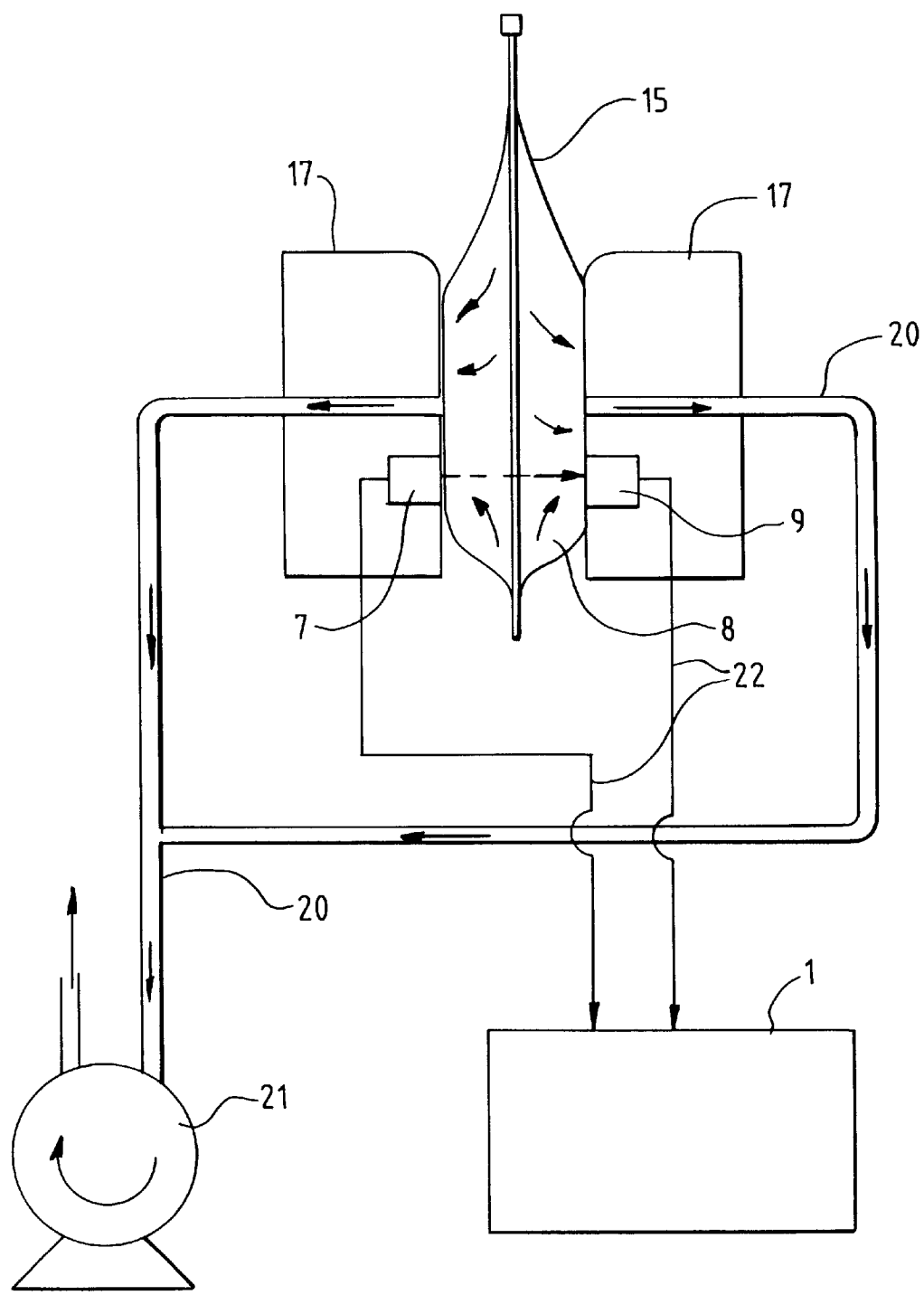
FIG. 4 is a schematic longitudinal centrally located cross-sectional view through the test apparatus of FIG. 3.

As illustrated in FIG. 4, the vacuum lines 20 are connected to a vacuum pump 21 so that as the bag 15 is passed between the housing 17, the sheet material of the windows 16 is held in close contact with the operating surface of the transducers 7, 9. A pair of electrical leads 22 connects the transducers 7, 9 to the electric circuit 1 of FIG. 1.

A second embodiment of the present invention will now be described with reference to FIGS. 5 to 7. The test apparatus 30 of FIGS. 5 and 6 consists of a generally rectangular base 31 mounted on four legs 32. Hinged to the base 31 is a lid 33. In the closed position illustrated in FIG. 6, the lid 33 and bottom 34 of the base 31 are substantially parallel. Centrally mounted within the bottom 34 is a transducer 35 which is arranged to face a receiving transducer 36 centrally mounted in the lid 33. Typically, the transducers are piezoelectric transducers incorporating PZT-4 (a lead zirconium titanate compound).

Figure 6:
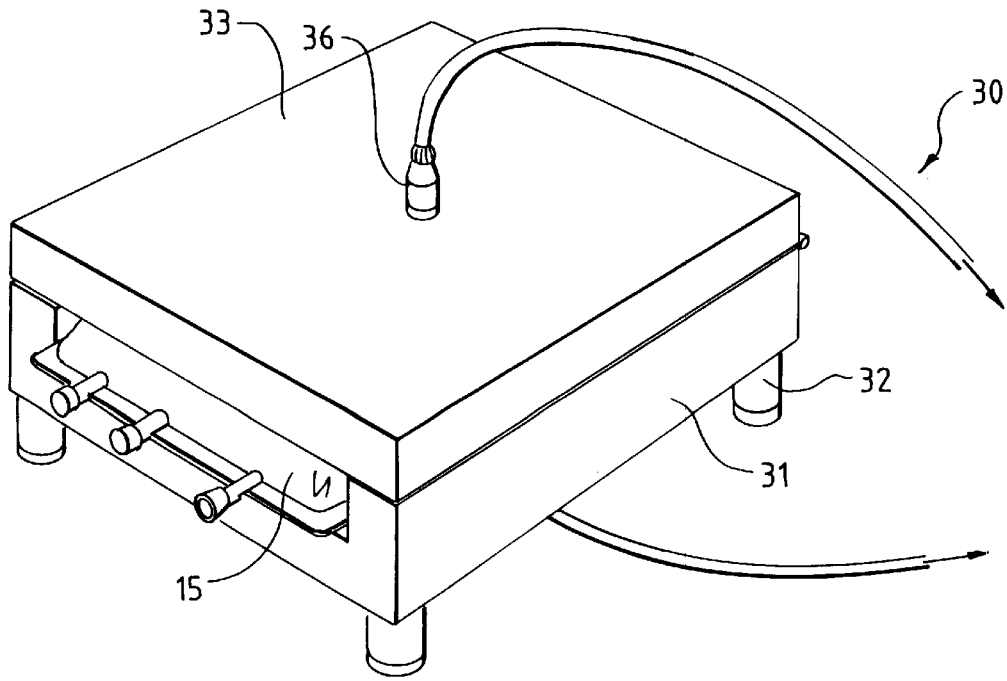
FIG. 6 is a similar view to FIG. 5 but showing the apparatus containing a bag of blood or like-liquid.

As indicated in FIG. 6, the blood sample 8 which is contained within the plastic bag 15 is able to be "clamped" between the bottom 34 and lid 33 so that the bag 15 to some extent bulges from the test apparatus 30. This provides a clear indication that the bag 15 more than fills the volume between the lid 33 and bottom 34. This therefore ensures that the plastic material of the bag 15 is abutting the transducers 35, 36 and that there are no air bubbles, or the like, in the blood in the region between the two transducers 35, 36. Preferably, an ultrasonic coupling liquid is used to wet the outside surfaces of the bag 15 in the vicinity of the transducers 35, 36 so as to ensure good ultrasonic coupling between the transducers 35, 36 and the bag 15. The preferred coupling liquid is distilled water.

Alternatively, the test apparatus can have a circular or half-spherical bottom portion. It also is possible to incorporate a small chamber-like insert for small volume tests (eg. non-blood pack type measurements).

Figure 5:
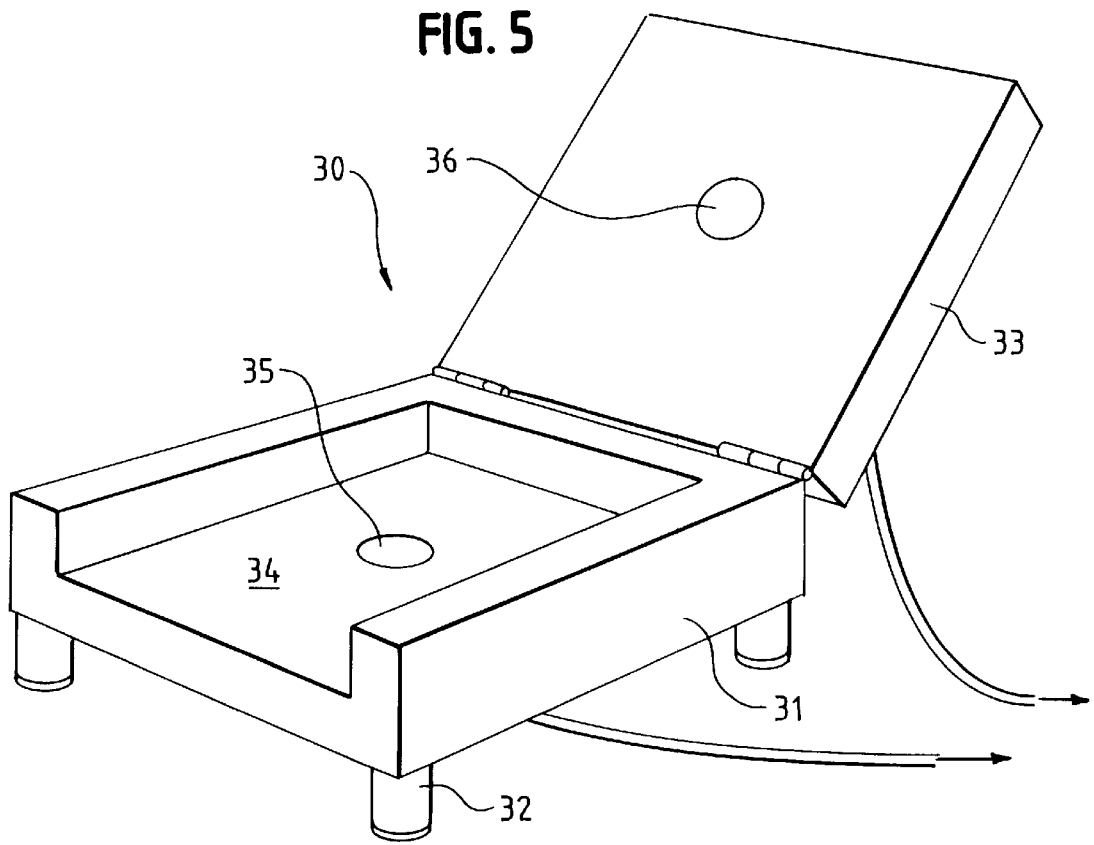
FIG. 5 is a schematic perspective view of test apparatus in accordance with a second embodiment, the apparatus being open.
Figure 7:
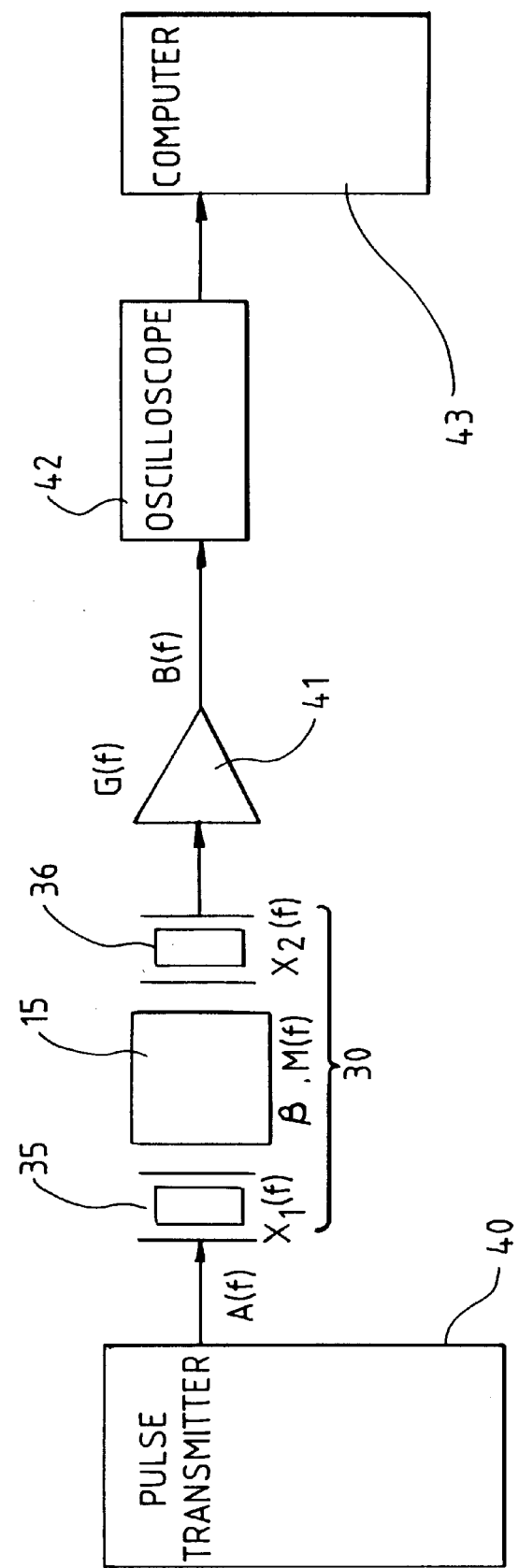
FIG. 7 is a block diagram of the test circuit for use with the apparatus of FIGS. 5 and 6, FIGS. 8 to 11 are plot of test results obtained by the apparatus of FIGS. 5 to 7, FIGS. 12 and 13 respectively are a perspective view of, and a longitudinal cross-section through, a testing syringe of a third embodiment.

Turning now to FIG. 7, the electronics connected to the test apparatus 30 of FIGS. 5 and 6 is schematically illustrated in FIG. 7. The transmit transducer 35 is connected to a pulse transmitter 40 via an internal impedance matching network. The receive transducer 36 is connected to a very low noise broad band amplifier 41, the output of which is connected to a fast analogue to digital converter (ADC) 42 (which samples at up to 500 MS/s), such as a storage oscilloscope. The digital output of the oscilloscope 42 is connected to a personal computer 43 for the purposes of data-logging and signal processing, including fast Fourier transforming and deconvolution.

The sampling oscilloscope 42, preferably, time gates the output from the received transducer 36 so as to eliminate signals derived from echoes from the rear wall of the transmit transducer 35, and like reflections. The amplitude of the received signal, typically of the order of Five volts, is used to calculate the ultrasound absorption coefficient of the bag 15 and its contents.

A short pulse contains a broad range of frequencies, and very short pulses have a very wide bandwidth. It has been determined that the pulse width preferably should be ≦10 ns, and the pulse have a rise time of ≦1 ns.

The spectrum of the received waveform is calculated by a fast Fourier transform of samples of the received waveform. The amplitude spectrum of the received waveform is deconvolved from the transfer functions of the transducers, cabling, and amplifier, yielding a set of amplitudes representing the frequency dependent absorption of the medium. Given these amplitudes, the absorption coefficient can be calculated as stated above at each frequency.

The non-ideal transfer functions of the transducers 35,41 and the other distorting influences in the measurement system can be removed by deconvolution performed in the frequency domain.

As shown in FIG. 7, the electrical output of the pulser 40, A(f), is available at the transducer terminals and the output of the amplifier, B(f), is sampled by the oscilloscope 42.

The transfer function of the transmitting transducer 35, $X_1(f)$ will convert the voltage on its terminals, A(f), to a velocity on its front face with some frequency dependent distortion. The transfer function of the medium, T(f), is composed of the frequency independent bulk modulus of the medium $\beta$, which converts velocity to pressure, and the absorption of the medium, M(f), which reduces the amplitude of the pressure as a function of frequency and distance. The pressure at the input side of the cell 15, $P_0(f)$, is attenuated by absorption in the medium so that the pressure at the output side of the cell is reduced.

The overall transfer function of the measurement system is:

$$B(f) = X_1(f) \cdot \beta \cdot M(f) \cdot X_2(f) \cdot G(f) \cdot A(f) \qquad 5$$

Rearranging for M(f):

$$M(f) = \frac{B(f)}{X_1(f) \cdot \beta \cdot X_2(f) \cdot G(f) \cdot A(f)} \qquad 6$$

The aim of the measurement is to extract $\alpha(f)$ and present it in a useful form:

$$\alpha(f) = -\frac{1}{d} \ln[M(f)] \qquad 7$$

To do so the transfer functions $X_1(f)$, $X_2(f)$ and $G(f)$ must be determined. If $\beta$ and M(f) are known, say $\beta'$ and M'(f), then the combination of $X_1(f), X_2(f)$ and $G(f)$ can be determined from:

$$X_1(f) \cdot X_2(f) \cdot G(f) = \frac{B'(f)}{T'(f) \cdot A'(f)} \qquad 8$$

where A'(f) and B'(f) are the input and output voltages respectively measured with medium T' in the cell and $T'(f) = \beta' \cdot e^{-\alpha'(f) \cdot d}$ is the transfer function of the medium T'. Both $\beta'$ and $\alpha'$ can be found in published data (eg. Kay, G. W. C. and Laby, T. H., Tables of Physical and Chemical Constants, Longman Scientific & Technical Publication Limited) for a large number of media. If the transfer functions are time invariant, then this value can be calculated before the actual measurement, then used to compensate for the transducers, cabling, and amplifier:

$$M(f) = \frac{B(f) \cdot A'(f) \cdot T'(f)}{\beta \cdot A(f) \cdot B'(f)} \qquad 9$$

If the electrical input voltage A(f) is time invariant and is not affected by the medium in the cell (principally loading effects due to the mass of the medium), then A'(f) will be equal to A(f) so:

$$M(f) = \frac{B(f)}{\beta} \cdot \frac{T'(f)}{B'_i(f)} \frac{B(f)}{\beta} \cdot \frac{T'(f)}{B'(f)} \qquad 10$$

The elements on the right hand side of the equation above are collected in two distinct groups. B(f) and P are associated with the medium being measured, while T'(f) and B'(f) are associated with the reference medium. The elements associated with the reference medium will not change from measurement to measurement and so can be collected together as a single correction function, C(f).

The correction function is then:

$$C(f) = \frac{T'(f)}{B'(f)} \qquad 11$$

and so the absorption function for the medium can be calculated as:

$$\alpha(f) = -\frac{1}{d} \cdot \ln\left[\frac{B(f)}{\beta} \cdot C(f)\right] \qquad 12$$

Figure 8:
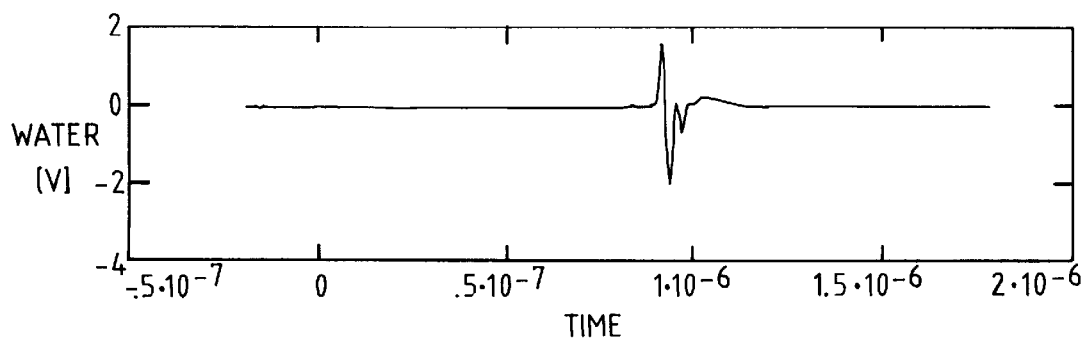
Figure 9:
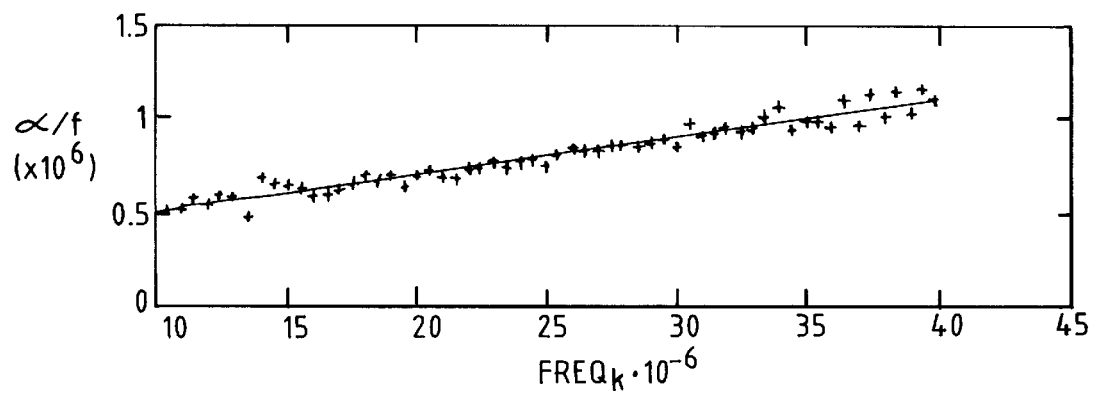

FIG. 8 shows a typical time trace of a received pulse passing through the medium of water. The received data is transformed into the Fourier domain, then deconvolved to account for the transfer function of the transducers and amplifier. The absorption coefficient then is calculated at the function of frequency, then scaled with frequency. The slope of the initial portion of the frequency scale absorption coefficient can then be obtained as a reference value. FIG. 9 shows an example of the frequency-scaled absorption coefficient for water.

Figure 10:
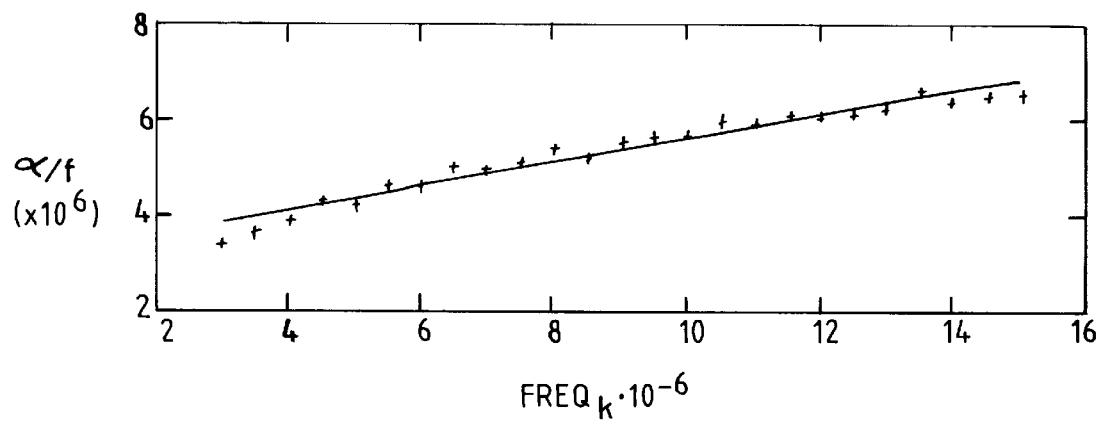
Figure 11:
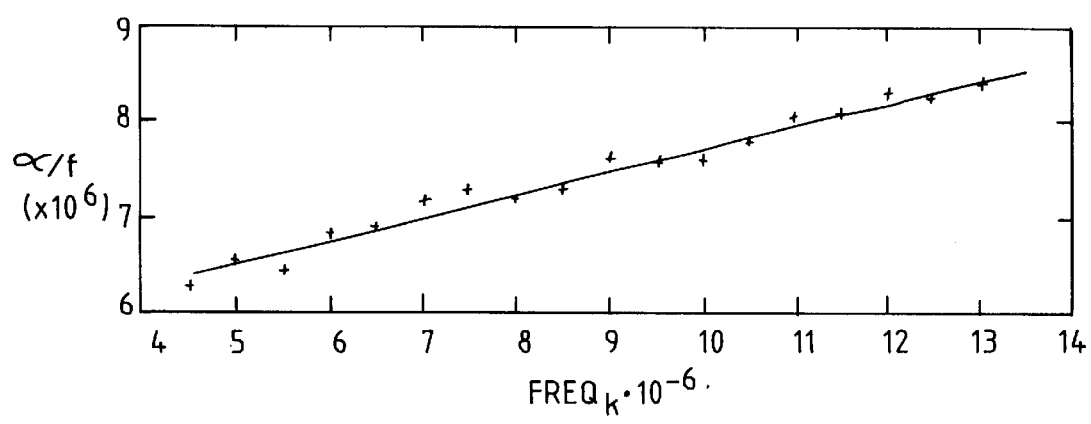

A similar process occurs for the red blood cells under test. A number of samples are taken to be averaged. FIGS. 10 and 11 respectively show a plot of frequency scaled absorption coefficient with frequency for fresh blood and for heat hardened blood. The heat hardened blood is constituted by fresh blood that has been subjected to the treatment at 50° C. for a period of time to cause embrittlement of the red blood cells, and thus simulate ageing. Over five actual examples, the mean value of the slope for fresh blood was 2.5 ($\times 10^{-13}$), while for heat-hardened blood over five similar samples, the mean value of the slope was 2.1 ($\times 10^{-13}$).

The determination of whether a sample of blood is sufficiently fresh to retain in storage for a further period of time or to use in a transfusion can be based on sets of empirical data gathered over time. In the present case, a value below 2.3 may be rejectable.

The two embodiments described above will enable a determination of the condition of red blood cells in a sample to be made in less than one minute, thus making the methodology and apparatus well suited for commercial use in hospitals, blood banks, and the like. Each unit of blood, thus, can be individually and quickly tested, resulting in a significant saving in acceptable blood that otherwise may be discarded.

Figure 12:
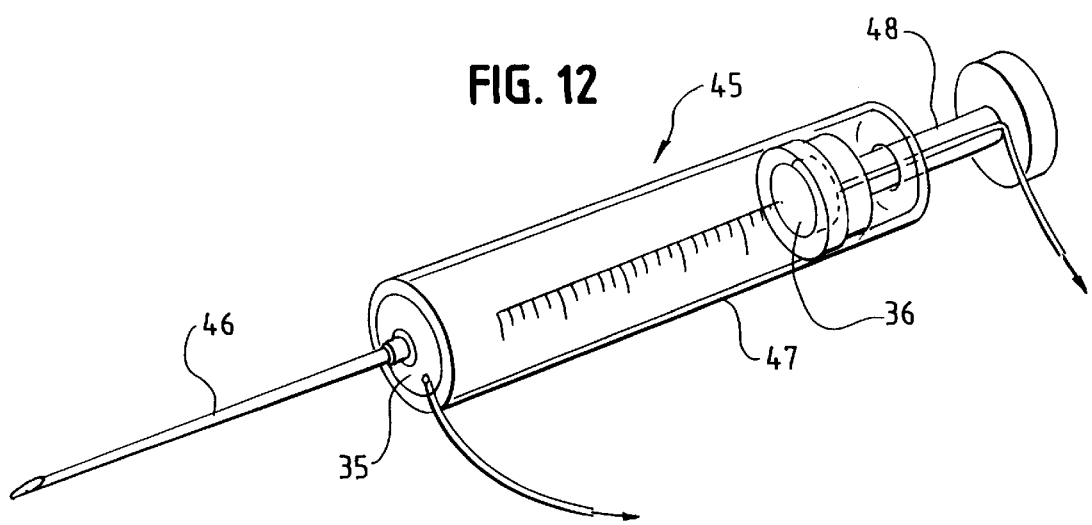
Figure 13:
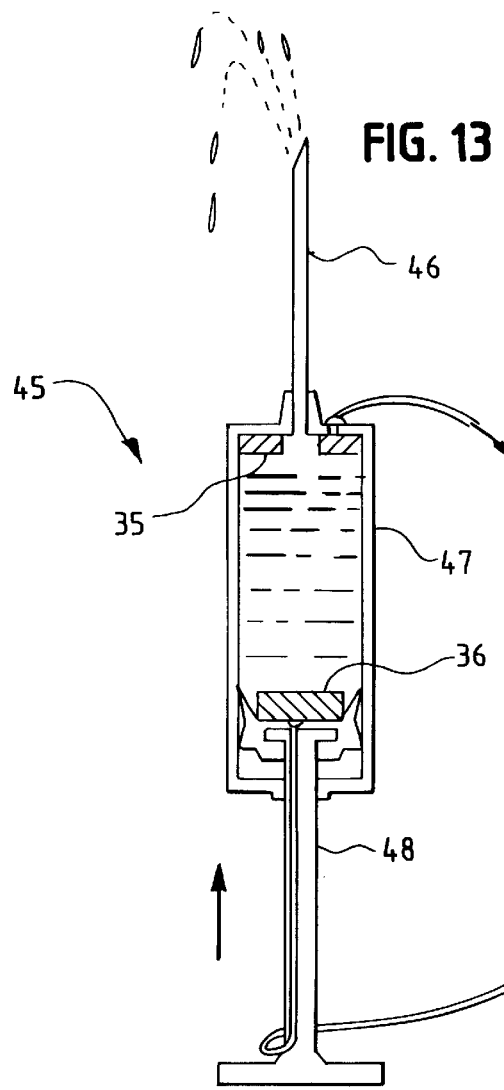
Figure 14:
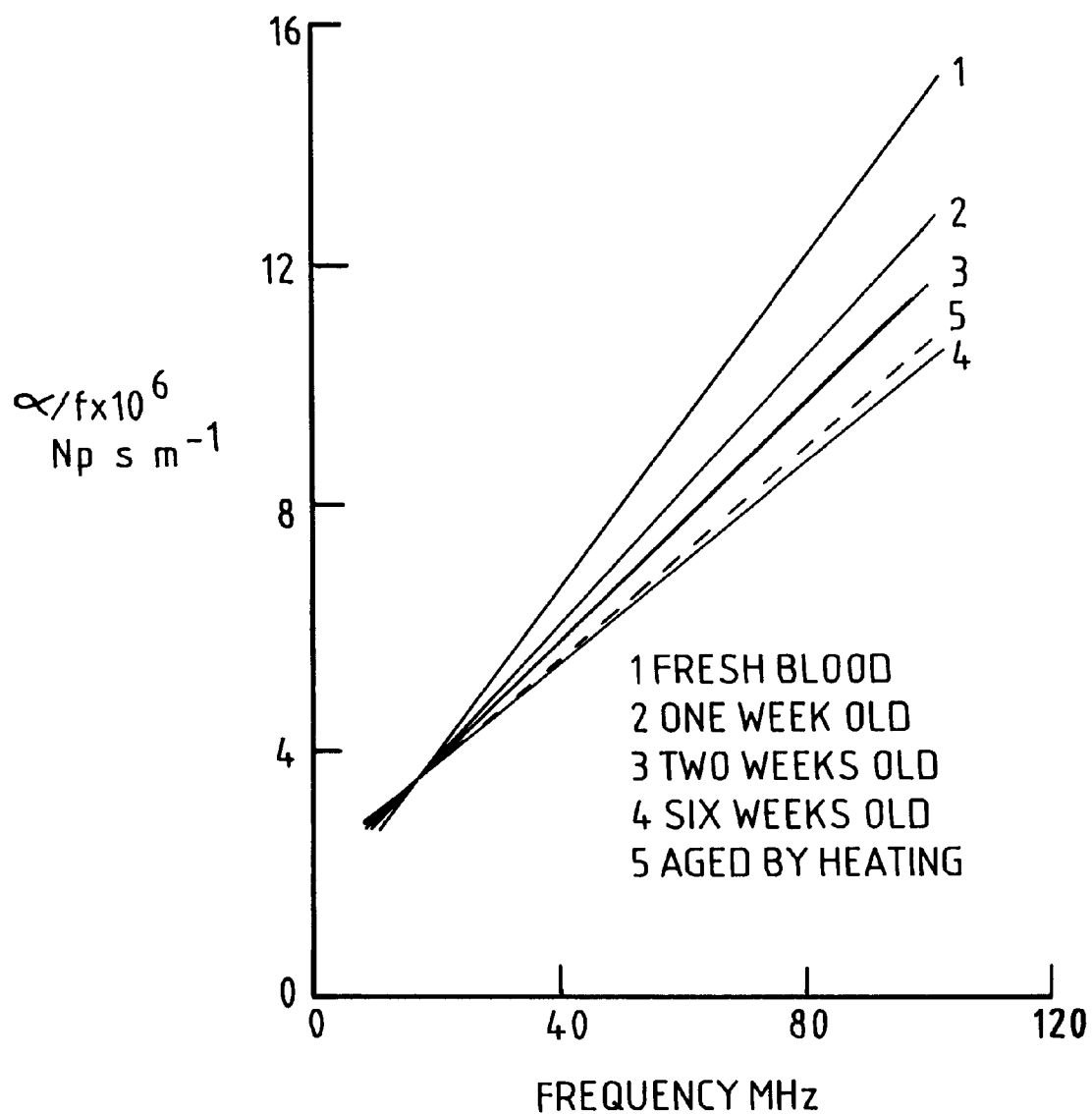
FIG. 14 is a prior art plot of frequency-scaled absorptivity versus frequency.

Turning now to FIGS. 12 and 13, a test syringe 45 constitutes a third embodiment of the present invention. The syringe 45 has a substantially conventional needle 46, barrel 47, and plunger 48. However, located at the needle end of the barrel 47 is an annular transmitting transducer 35 and carried on the plunger 48 is a disc shaped receiving transducer 36. It will be apparent to those skilled in the medical arts, that the syringe 45 can be used to take a blood sample and, as illustrated in FIG. 10, with the needle 46 elevated, the plunger 48 can be moved towards the needle 46 so as to remove any air bubbles which may have been included within the barrel 47. After this preliminary step has been taken, the transducers 35, 36 can be used to measure the properties of the blood contained within the barrel 47. Typically, the volume of the barrel 47 is approximately 3 ml.

We claim:

1. A method for measuring the deformability of particles suspended in a contained medium, said method comprising the steps of:

locating said contained medium between a pair of ultrasonic transducers spaced apart at a predetermined distance, applying an input electrical pulse to one of said transducers to transmit an ultrasonic signal through said medium, said input electrical pulse comprising or containing a range of frequencies, receiving said ultrasonic signal with the other of said transducers to generate a resultant output electrical signal, processing said output electrical signal with the other of said transducers to generate a resultant output electrical signal, and p1 processing said output electrical signal for all of said frequencies in said range, simultaneously calculating n absorption coefficient values for the particle as a function of frequency ($\alpha_n(f_n)$), scaling the absorption coefficient values by the respective frequency ($\alpha_n(f_n)/(f_n)$), and, for at least two of said values, calculating the ratio of the difference between the frequency-scaled absorption value and the difference between the respective frequency ($\Delta((f_n)/(f))_{1,2}/\Delta f_{1,2}$).

2. The method of claim 1, wherein the input signal is a frequency swept signal which is swept from one end of said range of frequencies to the other.

3. The method of claim 2, whereby the input signal is a square pulse, the harmonic content of which contains the desired range of frequencies.

4. The method of claim 3, whereby the square pulse has a width $\leq 10$ ns.

5. The method of claim 4, whereby the square pulse has a time of $\leq 1$ ns.

6. The method of claim 1, comprising the further step of comparing said calculated ratio with a reference value to determine whether the particles have or have not the desired deformability.

7. The method of claim 1, whereby said particles are red blood cells.

8. Apparatus for measuring the deformability of particles suspended in a contained medium and comprising:

a pair of opposed ultrasonic transducers spaced apart at a predetermined distance and between which a sample of said contained medium can be located, a signal generator for applying an input electrical pulse to one of said transducers to transmit an ultrasonic signal through said medium, said input electrical pulse comprising a range of frequencies, the propagated signal being received by the other of said transducers to generate an output electrical signal, and signal processing means for receiving the output electrical signal and all of said frequencies in said range, simultaneously calculating n absorption coefficient values for the particles as a function of frequency ($\alpha_n(f_n)$), scaling the absorption coefficient values by the respective frequency ($\alpha_n(f_n)/f_n$) and calculating the ratio, for at least two of n said values, of the difference between the frequency-scaled absorption value and the difference between the respective frequency ($\Delta(\alpha(f)/f)_{1,2}/\Delta f_{1,2}$).

9. The apparatus of claim 8, wherein the signal generator generates a frequency swept signal which is swept from one end of said range of frequencies to the other.

10. The apparatus of claim 8, wherein the signal generator generates a square pulse, the harmonic content of which contains the desired range of frequencies.

11. The apparatus of claim 10, wherein the square pulse has a pulse width $\leq 10$ ns.

12. The apparatus of claim 11, wherein the square pulse has a rise time of $\leq 1$ ns.

13. The apparatus of claim 8, wherein said signal processing means further stores a reference value against which said calculated ratio is compared to determine whether the particles have or have not the desired deformability.

14. The apparatus of claim 8, wherein said particles are red blood cells.

15. A method for measuring the acoustic absorption of suspended red blood cells, the method comprising the steps of:

locating said red blood cells between a pair of ultrasonic transducers spaced apart at a predetermined distance, applying an input electrical pulse to one of said transducers to transmit an ultrasonic signal through said suspended red blood cells in a contained medium, said input electrical pulse having a range of frequencies, receiving an ultrasonic signal with the other of said transducers to generate a resultant output electrical signal, and processing said output electrical signal simultaneously and for all of said frequencies in said range, calculating the absorption coefficients, $\alpha$, for one or more frequencies, said absorption coefficients being inversely proportional to the separation of the transducers and proportional to the natural logarithm of the amplitude of said output electrical signal.

16. The method of claim 15, wherein said input electrical signal is a square pulse, the harmonic content of which contains the desired range of frequencies.

17. The method of claim 16, wherein said range of frequencies has the highest lower bound of 10 MHz and the lowest upper bound of 40 MHz.

* * * * *

UNITED STATES PATENT AND TRADEMARK OFFICE
CERTIFICATE OF CORRECTION

PATENT NO.: 5,952,560

DATED : September 14, 1999

INVENTOR(S): Anthony F. Collins, Nicholas Bajenov, Peter John Cusak

It is hereby certified that error appear(s) in the above-identified patent and that said Letters Patent is hereby corrected as shown below:

Column 7, line 62, "P" should be --ß--.

Column 9, line 10, "p1" should be deleted and a new subparagraph should begin with "processing said output electrical signal".

Column 9, line 28, "rise" should be inserted between "a" and "time".

Signed and Sealed this

Twenty-sixth Day of December, 2000

*Attest:*

Q. TODD DICKINSON

*Attesting Officer*      *Director of Patents and Trademarks*